United States Patent
Singh

(10) Patent No.: US 8,838,421 B2
(45) Date of Patent: Sep. 16, 2014

(54) METHOD AND CIRCUIT FOR CALCULATING SENSOR MODELLING COEFFICIENTS

(75) Inventor: Mahendra Pal Singh, Noida (IN)

(73) Assignee: Freescale Semiconductor, Inc.

( * ) Notice: Subject to any disclaimer, the term of this patent is extended or adjusted under 35 U.S.C. 154(b) by 442 days.

(21) Appl. No.: 13/249,271

(22) Filed: Sep. 30, 2011

(65) Prior Publication Data

US 2013/0085725 A1    Apr. 4, 2013

(51) Int. Cl.

| | |
|---|---|
| *G06F 17/10* | (2006.01) |
| *G01D 18/00* | (2006.01) |
| *G06F 17/50* | (2006.01) |
| *G01K 7/16* | (2006.01) |
| *G01K 7/25* | (2006.01) |
| *G01K 15/00* | (2006.01) |
| *G01N 21/27* | (2006.01) |

(52) U.S. Cl.
CPC ............ *G06F 17/5063* (2013.01); *G01D 18/00* (2013.01); *G01N 21/274* (2013.01); *G01K 7/16* (2013.01); *G01K 7/25* (2013.01); *G01K 15/005* (2013.01)
USPC .............................................. 703/2; 702/104

(58) Field of Classification Search
CPC ............ G01N 21/274; B65H 2557/61; F02D 2041/1433; G01D 18/00
USPC .............................................. 703/2; 702/104
See application file for complete search history.

(56) References Cited

U.S. PATENT DOCUMENTS

| 4,226,125 A | 10/1980 | Waugh |
| 4,788,521 A | 11/1988 | Johnson |
| 5,764,067 A | 6/1998 | Rastegar |
| 5,946,642 A | 8/1999 | Hedrick |
| 7,483,795 B2 | 1/2009 | Miller |
| 8,195,418 B2 | 6/2012 | Borenstein |
| 8,589,107 B2 | 11/2013 | Borenstein |
| 2006/0265167 A1 | 11/2006 | Larala |

OTHER PUBLICATIONS

Bernhard Klassen, "A method for tightly coupled thermal-electrical simulation", GMD-SET Institute, Nov. 8, 2007 8 pages.*
Wikipedia, "Newton's method", 12 pages, Sep. 5, 2010.*

* cited by examiner

Primary Examiner — David Silver
(74) Attorney, Agent, or Firm — Charles Bergere

(57) ABSTRACT

A method of calculating sensor modelling coefficients includes determining a preliminary coefficient value for a first sensor modelling coefficient, calculating a coefficient value for a further sensor modelling coefficient using the preliminary coefficient value for the first sensor modelling coefficient and a data measurement value, and calculating a refined coefficient value for the first sensor modelling coefficient using the calculated coefficient value for the further sensor modelling coefficient and the data measurement value.

11 Claims, 3 Drawing Sheets

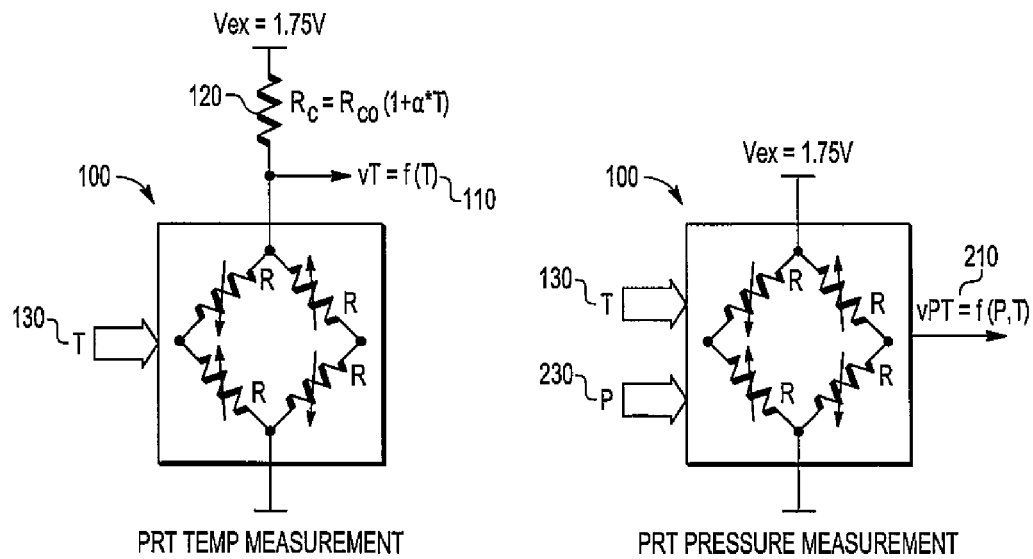
*FIG. 1*  *FIG. 2*
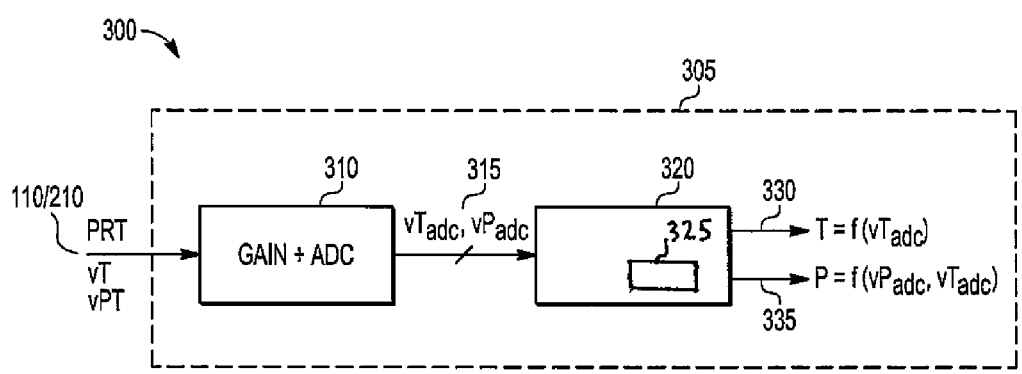
*FIG. 3*

METHOD AND CIRCUIT FOR CALCULATING SENSOR MODELLING COEFFICIENTS

CROSS-REFERENCE TO RELATED APPLICATIONS

The present application is related to U.S. patent application Ser. No. 13/249,256 filed Sep. 30, 2011, which has the same inventor and assignee.

BACKGROUND OF THE INVENTION

The present invention relates to a method and circuit for calculating sensor modelling coefficients such as for a pressure or temperature sensor.

In the field of sensor systems, for example pressure and/or temperature sensor systems, it is known for an output of a sensor device to be modelled using one or more equations, and for the output of such a sensor device to be dependent upon higher order input terms. For example, the output of a piezo resistive transducer is dependent upon pressure, as well as being dependent upon temperature terms that could be of higher order. Accordingly, in order to accurately model the characteristics of such sensors, it is necessary to calculate coefficients for the higher order terms.

A traditional approach to calculating such coefficients is to take multiple data readings, use the multiple data readings to establish multiple equations comprising just the unknown coefficients to be calculated, and to solve the equations to determine the coefficient values. A problem with this approach, at least in relation to sensor devices such as piezo resistive transducers is that typically the equation for modelling the characteristics of the sensor device may be of third order or higher. Accordingly, at least four temperature readings are required to solve for the coefficients. Furthermore, the output of such piezo resistive transducers is further dependent upon pressure, thereby requiring additional readings to be taken for different pressure settings. However, taking multiple data readings for different pressure settings in this manner for individual sensor systems is cost prohibitive. Furthermore, it can be cost prohibitive and technically challenging to modify sensors to have a lower order of variation with respect to pressure and/or temperature.

A known solution to this problem is to drop higher order terms from the equations, thereby removing the higher order coefficients and reducing the number of data readings required to calculate remaining coefficients. However, a problem with this solution is that the dropping of higher order terms from the equations can lead to inaccurate estimation of the curve for the sensor device, should the dropped terms have significant weight in terms of performance, and thus can lead to inaccurate modelling of the sensor device.

An alternative known solution to this problem is to use mean values for higher order coefficients, thereby reducing the number of data readings required to be taken. However, the characteristics of individual sensor devices can vary significantly from one fabrication lot to another. Accordingly, a problem with this solution is that the use of mean values for higher order coefficients may also lead to inaccurate estimation of the curve for sensor devices with characteristics that vary from those used to establish the mean values, and thus can also lead to inaccurate modelling of the sensor device. As such, in order for such mean values to be used to reliably and accurately model the characteristics of such sensors, tight design and fabrication tolerances for the sensor devices are required. However, such tight design and fabrication tolerances result in an increase in the costs of production and testing of the sensor devices.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

FIG. 1 illustrates a simplified circuit diagram of an example of a piezo resistive transducer configured in a first mode of operation.

FIG. 2 illustrates a simplified circuit diagram of an example of a piezo resistive transducer configured in a second mode of operation.

FIG. 3 illustrates a simplified block diagram of an example of part of a sensor system.

DETAILED DESCRIPTION

Figure 4:
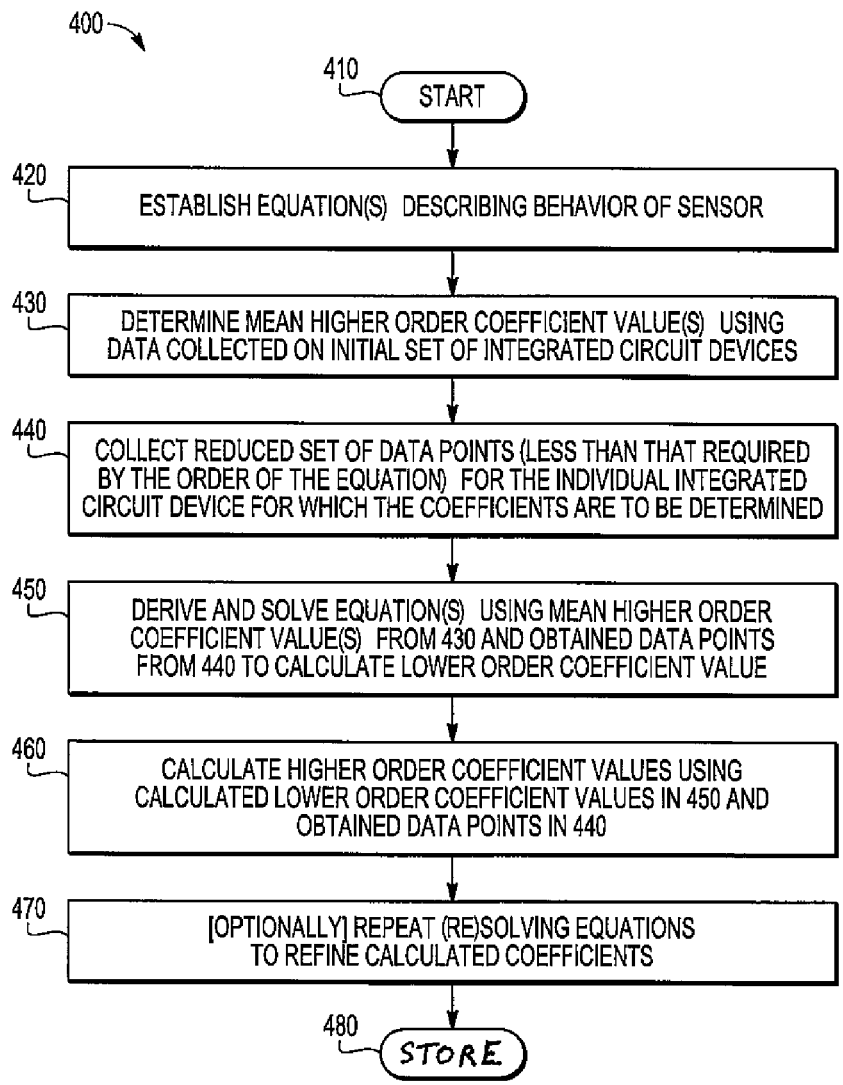
FIG. 4 illustrates a simplified flowchart of an example of a method of calculating sensor modelling coefficients in accordance with an embodiment of the present invention.

The present invention provides a method of calculating sensor modelling coefficients, an integrated circuit comprising at least one signal processing module arranged to calculate sensor modelling coefficients, a tangible computer program product having executable program code stored therein for calculating sensor modelling coefficients, and an integrated circuit device comprising a processing component arranged to generate sensor measurement values based at least partly on at least one sensor modelling coefficient calculated thereby as described in the accompanying claims. These and other aspects of the invention will be apparent from and elucidated with reference to the embodiments described hereinafter.

Examples of the present invention will now be described with reference to the accompanying drawings. In particular, examples of the present invention are herein described with reference to a temperature and/or pressure sensor comprising a piezo resistive transducer arranged to provide temperature and/or pressure measurements. However, it will be appreciated that the present invention is not limited to the particular embodiments herein described, and may be equally applied to alternative sensor arrangements for which equation coefficients are required to be determined. Furthermore, because the illustrated embodiments of the present invention may, for the most part, be implemented using electronic components and circuits known to those skilled in the art, details will not be explained in any greater extent than that considered necessary as illustrated below, for the understanding and appreciation of the underlying concepts of the present invention and in order not to obfuscate or distract from the teachings of the present invention.

Referring first to FIGS. 1 and 2, there are illustrated simplified circuit diagrams of examples of a piezo resistive transducer 100 configured within a sensor system, for example a temperature sensor system.

FIG. 1 illustrates a simplified circuit diagram of an example of the piezo resistive transducer 100, which in the illustrated example resembles a Wheatstone bridge, configured in a first mode of operation in order to provide a voltage signal vT 110 that is representative of temperature 130. In this first configuration, the piezo resistive transducer 100 is operably coupled in series with a resistance element 120 in order to provide a voltage divider configuration with the voltage signal vT 110 as an output thereof. Variations in temperature 130 cause representative variations in the resistance of the piezo resistive transducer 100, and therefor cause correspondingly representative variations in the voltage signal vT 110.

FIG. 2 illustrates a simplified circuit diagram of an example of the piezo resistive transducer 100 configured in a second mode of operation in order to provide a voltage signal vPT 210 that is representative of both pressure 230 and temperature 130. In this second configuration, an excitation voltage Vex 220 causes a differential output voltage vPT 210 that is a function of both pressure 230 and temperature 130. Variations predominantly in pressure 230 and to some extent in temperature 130 cause representative variations in the voltage signal vPT 210.

FIG. 3 illustrates a simplified block diagram of an example of part of a sensor system 300 to which the piezo resistive transducer 100 may be operably coupled, and to which the temperature and pressure voltage signals vT 110 and vPT 210, output by the piezo resistive transducer 100, may be provided. For the illustrated example, the piezo resistive transducer 100 is used to provide both the temperature and pressure voltage signals vT 110 and vPT 210. However, two separate sensors may be equally used to provide the voltage signals 110, 210. For example, a sensor independent of the piezo resistive transducer 100 may be used to provide a temperature voltage signal vT 110. The sensor system 300 may be implemented within an integrated circuit device 305, for example within an application specific integrated circuit (ASIC) or the like, and comprises, in some examples, an analogue to digital converter (ADC) 310 that receives the temperature and pressure voltage signals vT 110 and vPT 210 and outputs digital representations ($vT_{ADC}$ and $vP_{ADC}$ respectively) 315 thereof. The digital representations 315 of the temperature and pressure voltage signals are then provided to a processing component, which in the illustrated example comprises a data path 320 having a memory element 325, which processes the temperature and pressure voltage values 315 to generate estimated temperature and pressure values 330, 335. The memory element 325 is used to store intermediate values, coefficients, and estimated values, among other data, as will be understood by those of skill in the art.

In one embodiment, the piezo resistive transducer 100 is initially configured to operate in the first mode of operation and to provide the voltage signal vT 110 that is representative of temperature to the ADC component 310, which in turn outputs a digital representation $T_{adc}$ 315 of the temperature voltage signal. The piezo resistive transducer 100 is then configured to operate in the second mode of operation and to provide the voltage signal vPT 210 that is representative of temperature and pressure to the ADC component 310, which in turn outputs a digital representation $P_{adc}$ 315 of the pressure voltage signal. The data path 320 may then process the digital representations 315 of the temperature and pressure voltage signals in order to generate an estimated temperature value 330 and an estimated pressure value 335. The 'data path 320' may be a digital signal processor (DSP) or similar circuit. The order in which the digital representations of the temperature and pressure voltage signals 315 are processed may be interchanged, and sampling of the temperature and pressure voltage signals vT 110 and vPT 210 may be performed substantially independent. For example, the data path 320 may be arranged to generate the estimated temperature value 330 based on a first sensor modelling equation, such as shown in Equation 1 below:

$$T = cT_0 + cT_1 \cdot T_{adc} + cT_2 \cdot T_{adc}^2 + cT_3 \cdot T_{adc}^3 + cT_4 \cdot T_{adc} \cdot P_{adc} + cT_5 \cdot P_{adc}$$ [Equation 1]

Where: $cT_i$ comprises a first set of sensor modelling coefficients. Similarly, the data path 320 may be arranged to generate the estimated pressure value 335 based on a second modelling equation, such as shown in Equation 2 below:

$$P = C_0 + C_1 \cdot P_{adc} + C_2 \cdot T + C_3 \cdot P_{adc} \cdot T$$ [Equation 2]

Where: $C_i$ comprises a second set of sensor modelling coefficients.

Thus, in this example, the data path 320 may first generate an estimate of the temperature T 330 using Equation 1 above, with parameters of the digital representations 315 of the temperature and pressure voltage signals $T_{adc}$ and $P_{adc}$, and the first set of sensor modelling coefficients $cT_i$. Having generated an estimate of the temperature T 330, the data path 320 may then generate an estimate of the pressure P 335 using Equation 2 above, with parameters of the digital representation 315 of the pressure voltage signal $P_{adc}$, the estimate of the temperature T and the second set of sensor modelling coefficients $C_i$.

In order to accurately model the characteristics of sensor devices, such as the piezo resistive transducer 100 of FIGS. 1 and 2, it is important to calculate all coefficients that have significant weight in terms of performance, which may be of third order or higher. For the above example, Equation 1 comprises an expression of temperature as a function of the temperature voltage signal $T_{adc}$ of third order. As such, a minimum of four separate temperature readings would traditionally be required to establish derivative equations from Equation 1 comprising just the unknown coefficients to be calculated, and to solve the equations to determine the required coefficient values. However, taking multiple data readings in this manner for individual sensor systems is cost prohibitive. Furthermore, the output of such a piezo resistive transducer 100 is further dependent upon pressure, requiring additional readings to be taken for different pressure settings.

Referring now to FIG. 4, a simplified flowchart 400 of an example of a method of calculating sensor modelling coefficients, such as may be used within, say, the data path 320 of the sensor system 300 in order to generate sensor measurement values 330, 335 based on voltage signals vT 110 and vPT 210 output by the piezo resistive transducer 100, is shown.

The method comprises defining at least one preliminary coefficient value for at least a first sensor modelling coefficient, calculating at least one coefficient value for at least one further sensor modelling coefficient using the at least one preliminary coefficient value for the at least first sensor modelling coefficient and at least one data measurement value, and calculating at least one refined coefficient value for the at least first sensor modelling coefficient using the at least one calculated coefficient value for the at least one further sensor modelling coefficient and the at least one data measurement value.

In greater detail, the example method illustrated in FIG. 4 starts at 410 and moves on to 420 where one or more equations describing the behaviour of a sensor to be modelled are established; for example such as Equations 1 and 2 describing the behaviour of the piezo resistive transducer 100 above. Sensor modelling equations, such as Equations 1 and 2 above, may be established using a least mean square (LMS) method or otherwise during initial modelling of the sensor 100.

Next, at 430, one or more preliminary coefficient values is/are determined for one or more (initial) sensor modelling coefficients within the established equation (s). For example, and as illustrated in FIG. 4, such preliminary coefficient value(s) may be determined for one or more higher order sensor modelling coefficients within the established equations. Such preliminary coefficient value(s) may be determined using data collected on, say an initial set of integrated circuit devices. For example, such a mean coefficient value may be determined using a Least Mean Square (LMS) algorithm or the like.

The method then moves on to 440, where one or more data points comprising one or more data measurement values are obtained for the individual integrated circuit device 305, for which actual coefficients are to be determined. In particular, for some example embodiments, a reduced set of data points may be obtained as compared with some traditional methods of calculating sensor modelling coefficients. For example, such data points may be obtained by way of taking, say, temperature and/or pressure 330, 335 readings that are output by the piezo resistive transducer 100 under known conditions.

Derivative equations may then be derived from the equations previously established at 420 using the preliminary coefficient value(s) from 430 and the (reduced set) of obtained data points from 440. The derivative equations may then be solved to calculate coefficient values for one or more remaining sensor modelling coefficients within the established equation(s); for example for one or more lower order sensor modelling coefficients. For example, in the case of Equation 1 above, preliminary coefficient values may be determined for the coefficients: $cT_3$ $cT_4$ and $cT_5$. In this manner, the derivative equations may be solved to calculate coefficient values for the coefficients: $cT_0$, $cT_1$, $cT_2$ and $cT_5$. Thus, the highest order in this derivative set of equations may be reduced to two, thereby reducing the number of actual data points to be collected for calculation of coefficients. Thus, by using one or more preliminary coefficient values in this manner, coefficients may be determined using only a reduced set of data points.

However, since the coefficient values used for, in the above example, the higher order coefficients are only preliminary, for example based on mean coefficient values, a resulting estimation of the curve for the sensor device (e.g. the piezo resistive transducer 100 in the above example) will be inaccurate for individual devices with characteristics that vary from those used to establish, in this example, the mean values, which were based on an initial set of, say, integrated circuit devices, and thus can lead to inaccurate modelling of the sensor device.

Thus, for the example method illustrated in FIG. 4, having derived and solved the derivative equations from the equations previously established at 420 using the preliminary coefficient value(s) and the (reduced set) of obtained data points, the method moves on to 460 where further derivative equations are derived from the equations previously established at 420 using the obtained data points and the coefficient values for the 'one or more remaining sensor modelling coefficients' (e.g. the lower order coefficients in the above example) calculated in 450. These further derivative equations may then be solved to recalculate refined coefficient values for the one or more initial sensor modelling coefficients which were initially assigned in 430 (e.g., the higher order coefficients in the above example). These refined coefficient values for the initial sensor modelling coefficients may thus be used to replace the preliminary coefficient values therefor. Thus, since these refined coefficient values for the initial sensor modelling coefficients have been calculated at least partly based on the obtained data points, a resulting estimation of the curve for the sensor device (e.g. the piezo resistive transducer 100 in the above example) will be more accurate for individual devices with characteristics that vary from, say, some initial integrated circuit devices used to establish, in this example, the mean values, and thus can lead to a more accurate modelling of the sensor device.

As illustrated generally at 470, in some embodiments, further derivative equations may be derived and solved using previously calculated coefficient values. For example, further derivative equations may be derived using the obtained data points and the refined coefficient values calculated in 460, and solved to calculate refined coefficient values for, in the above example, the lower order coefficients. In this manner, the coefficient values may be iteratively refined to improve the accuracy thereof if desired. Step 480 indicates that the coefficients are stored in the memory element 325. As will be understood by those of skill in the art, intermediate calculated values and data also may be stored in the memory element 325.

Advantageously, calculating sensor modelling coefficients as described above in accordance with some example embodiments of the present invention may enable a reduction in data collection and the associated costs therefor, as well as enabling a reduction in the effect of variation of coefficient values across individual sensor devices and/or across fabrication lots of sensor devices. In addition, by enabling a reduction in the effect of such variation, design and fabrication tolerances for the sensor devices may be eased, enabling the costs thereof to be reduced.

Figure 5:
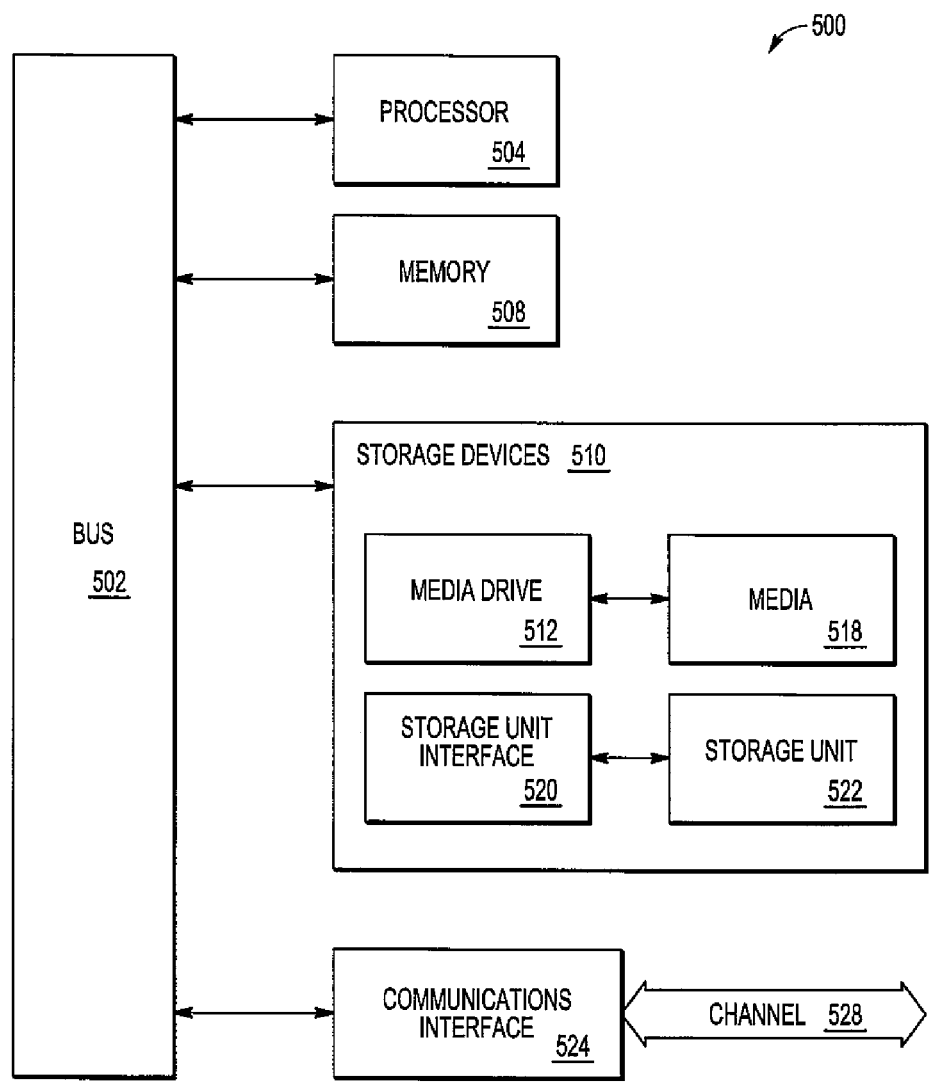
FIG. 5 illustrates an example of a computing system in accordance with an embodiment of the present invention.

Referring now to FIG. 5, there is illustrated an example of a typical computing system 500 that may be employed to implement signal processing functionality in embodiments of the invention, and in particular may be employed to implement at least part of the method of FIG. 4. Computing systems of this type may be used in desktop computers, workstations etc. Those skilled in the relevant art will also recognize how to implement the invention using other computer systems or architectures. Computing system 500 may represent, for example, a desktop, laptop or notebook computer, hand-held computing device (PDA, cell phone, palmtop, etc.), mainframe, server, client, or any other type of special or general purpose computing device as may be desirable or appropriate for a given application or environment. Computing system 500 can include one or more signal processing modules, such as a processor 504. Processor 504 can be implemented using a general or special-purpose processing engine such as, for example, a microprocessor, microcontroller or other control module. In this example, processor 504 is connected to a bus 502 or other communications medium.

Computing system 500 can also include a main memory 508, such as random access memory (RAM) or other dynamic memory, for storing information and instructions to be executed by processor 504. Main memory 508 also may be used for storing temporary variables or other intermediate information during execution of instructions to be executed by processor 504. Computing system 500 may likewise include a read only memory (ROM) or other static storage device coupled to bus 502 for storing static information and instructions for processor 504.

The computing system 500 may also include information storage system 510, which may include, for example, a media drive 512 and a removable storage interface 520. The media drive 512 may include a drive or other mechanism to support fixed or removable storage media, such as a hard disk drive, a floppy disk drive, a magnetic tape drive, an optical disk drive, a compact disc (CD) or digital video drive (DVD) read or write drive (R or RW), or other removable or fixed media drive. Storage media 518 may include, for example, a hard disk, floppy disk, magnetic tape, optical disk, CD or DVD, or other fixed or removable medium that is read by and written to by media drive 512. As these examples illustrate, the storage media 518 may include a computer-readable storage medium having particular computer software or data stored therein.

In alternative embodiments, information storage system 510 may include other similar components for allowing computer programs or other instructions or data to be loaded into computing system 500. Such components may include, for example, a removable storage unit 522 and an interface 520, such as a program cartridge and cartridge interface, a removable memory (for example, a flash memory or other removable memory module) and memory slot, and other removable storage units 522 and interfaces 520 that allow software and data to be transferred from the removable storage unit 518 to computing system 500.

Computing system 500 can also include a communications interface 524. Communications interface 524 can be used to allow software and data to be transferred between computing system 500 and external devices. Examples of communications interface 524 can include a modem, a network interface (such as an Ethernet or other NIC card), a communications port (such as for example, a universal serial bus (USB) port), a PCMCIA slot and card, etc. Software and data transferred via communications interface 524 are in the form of signals which can be electronic, electromagnetic, and optical or other signals capable of being received by communications interface 524. These signals are provided to communications interface 524 via a channel 528. This channel 528 may carry signals and may be implemented using a wireless medium, wire or cable, fiber optics, or other communications medium. Some examples of a channel include a phone line, a cellular phone link, an RF link, a network interface, a local or wide area network, and other communications channels.

In this document, the terms 'computer program product' 'computer-readable medium' and the like may be used generally to refer to media such as, for example, memory 508, storage device 518, or storage unit 522. These and other forms of computer-readable media may store one or more instructions for use by processor 504, to cause the processor to perform specified operations. Such instructions, generally referred to as 'computer program code' (which may be grouped in the form of computer programs or other groupings), when executed, enable the computing system 500 to perform functions of embodiments of the present invention. Note that the code may directly cause the processor to perform specified operations, be compiled to do so, and/or be combined with other software, hardware, and/or firmware elements (e.g., libraries for performing standard functions) to do so.

In an embodiment where the elements are implemented using software, the software may be stored in a computer-readable medium and loaded into computing system 500 using, for example, removable storage drive 522, drive 512 or communications interface 524. The control module (in this example, software instructions or executable computer program code), when executed by the processor 504, causes the processor 504 to perform the functions of the invention as described herein.

Accordingly, the invention may be implemented in a computer program for running on a computer system, at least including code portions for performing steps of a method according to the invention when run on a programmable apparatus, such as a computer system or enabling a programmable apparatus to perform functions of a device or system according to the invention.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system.

The computer program may be stored internally on computer readable storage medium or transmitted to the computer system via a computer readable transmission medium. All or some of the computer program may be provided on computer readable media permanently, removably or remotely coupled to an information processing system. The computer readable media may include, for example and without limitation, any number of the following: magnetic storage media including disk and tape storage media; optical storage media such as compact disk media (e.g. CD-ROM, CD-R, etc.) and digital video disk storage media; non-volatile memory storage media including semiconductor-based memory units such as FLASH memory, EEPROM, EPROM, ROM; ferromagnetic digital memories; MRAM; volatile storage media including registers, buffers or caches, main memory, RAM, etc.; and data transmission media including computer networks, point-to-point telecommunication equipment, and carrier wave transmission media, just to name a few.

A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output (I/O) devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the broader spirit and scope of the invention as set forth in the appended claims.

The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality. For example, in the example illustrated in FIG. 3 the ADC component 310 and data path 320 have been illustrated as separate logic blocks within the integrated circuit device. However, in some examples, that the functionality of the ADC component 310 and the functionality of the data path 320 may at least partly be implemented within a single functional element.

Any arrangement of components to achieve the same functionality is effectively 'associated' such that the desired functionality is achieved. Hence, any two components herein combined to achieve a particular functionality can be seen as 'associated with' each other such that the desired functionality is achieved, irrespective of architectures or intermediary components. Likewise, any two components so associated can also be viewed as being 'operably connected', or 'operably coupled', to each other to achieve the desired functionality.

Those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

The examples, or portions thereof, may implemented as soft or code representations of physical circuitry or of logical representations convertible into physical circuitry, such as in a hardware description language of any appropriate type. Also, the invention is not limited to physical devices or units implemented in non-programmable hardware but can also be applied in programmable devices or units able to perform the desired device functions by operating in accordance with suitable program code, such as mainframes, minicomputers, servers, workstations, personal computers, notepads, personal digital assistants, electronic games, automotive and other embedded systems, cell phones and various other wireless devices, commonly denoted in this application as 'computer systems'. However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms 'a' or 'an,' as used herein, are defined as one or more than one. Also, the use of introductory phrases such as 'at least one' and 'one or more' in the claims should not be construed to imply that the introduction of another claim element by the indefinite articles 'a' or 'an' limits any particular claim containing such introduced claim element to inventions containing only one such element, even when the same claim includes the introductory phrases 'one or more' or 'at least one' and indefinite articles such as 'a' or 'an.' The same holds true for the use of definite articles. Unless stated otherwise, terms such as 'first' and 'second' are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

The invention claimed is:

1. A method of calculating sensor modelling coefficients, the method comprising:
   determining at least one preliminary coefficient value for at least a first sensor modelling coefficient;
   calculating at least one coefficient value for at least one further sensor modelling coefficient using the at least one preliminary coefficient value and at least one data measurement value;
   calculating at least one refined coefficient value for the first sensor modelling coefficient using the at least one calculated coefficient value for the at least one further sensor modelling coefficient and the at least one data measurement value;
   storing the calculated refined coefficient in a sensor system for converting a digitized sensor signal to an estimated sensor output signal.

2. The method of claim 1, wherein the at least first sensor modelling coefficient comprises at least one first order coefficient and the at least one further sensor modelling coefficient comprises at least one second order coefficient, wherein the first order is higher than the second order.

3. The method of claim 1, wherein the method comprises determining, as the at least one preliminary coefficient value, at least one mean coefficient value for the at least first sensor modelling coefficient.

4. The method of claim 3, wherein the method comprises determining, as the at least one preliminary coefficient value, at least one least mean square coefficient value for the at least first sensor modelling coefficient.

5. The method of claim 1, further comprising solving at least one sensor modelling equation using the at least one preliminary coefficient value for the at least first sensor modelling coefficient and the at least one data measurement value to calculate the at least one coefficient value for the at least one further sensor modelling coefficient.

6. The method of claim 5, further comprising solving the at least one sensor modelling equation using the at least one calculated coefficient value for the at least one further sensor modelling coefficient and the at least one data measurement value to calculate the at least one refined coefficient value for the at least first sensor modelling coefficient.

7. The method of claim 1, wherein the method further comprises calculating at least one refined coefficient value for the at least one further sensor modelling coefficient using the at least one refined coefficient value for the at least first sensor modelling coefficient and at least one data measurement value.

8. The method of claim 1, further comprising modelling at least one of a temperature sensor and a pressure sensor using the stored value.

9. An integrated circuit comprising at least one signal processing module arranged to calculate sensor modelling coefficients and a memory for storing the calculated sensor modelling coefficients, the at least one signal processing module being arranged to:
   determine at least one preliminary coefficient value for at least a first sensor modelling coefficient;
   calculate at least one coefficient value for at least one further sensor modelling coefficient using the at least one preliminary coefficient value for the at least first sensor modelling coefficient and at least one data measurement value; and calculate at least one refined coefficient value for the at least first sensor modelling coefficient using the at least one calculated coefficient value for the at least one further sensor modelling coefficient and the at least one data measurement value.

10. A non-transitory tangible computer program product having executable program code stored therein for calculating sensor modelling coefficients for multiple sensor regions of operation, the program code operable for:

determining at least one preliminary coefficient value for at least a first sensor modelling coefficient;

calculating at least one coefficient value for at least one further sensor modelling coefficient using the at least one preliminary coefficient value for the at least first sensor modelling coefficient and at least one data measurement value; and calculating at least one refined coefficient value for the at least first sensor modelling coefficient using the at least one calculated coefficient value for the at least one further sensor modelling coefficient and the at least one data measurement value.

11. The tangible computer program product of claim 10, wherein the tangible computer program product comprises at least one of: a hard disk, a CD-ROM, an optical storage device, a magnetic storage device, a Read Only Memory, ROM, a Programmable Read Only Memory, PROM, an Erasable Programmable Read Only Memory, EPROM, an Electrically Erasable Programmable Read Only Memory, EEPROM, and a Flash memory.

* * * * *